US009616230B2

(12) United States Patent
Grandhe

(10) Patent No.: US 9,616,230 B2
(45) Date of Patent: Apr. 11, 2017

(54) SYSTEMS AND METHODS FOR PROGRAMMING A NEUROMODULATION SYSTEM

(71) Applicant: Boston Scientific Neuromodulation Corporation, Valencia, CA (US)

(72) Inventor: Sarvani Grandhe, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/569,155

(22) Filed: Dec. 12, 2014

(65) Prior Publication Data
US 2015/0165202 A1    Jun. 18, 2015

Related U.S. Application Data

(60) Provisional application No. 61/915,422, filed on Dec. 12, 2013.

(51) Int. Cl.
*A61N 1/00* (2006.01)
*A61N 1/36* (2006.01)
(Continued)

(52) U.S. Cl.
CPC ....... *A61N 1/36071* (2013.01); *A61N 1/0551* (2013.01); *A61N 1/36132* (2013.01); *A61N 1/36185* (2013.01); *A61N 1/37247* (2013.01)

(58) Field of Classification Search
USPC ......................................... 607/46
See application file for complete search history.

(56) References Cited

U.S. PATENT DOCUMENTS 5,938,690 A    8/1999 Law et al.
5,941,906 A    8/1999 Barreras, Sr. et al.
(Continued)

FOREIGN PATENT DOCUMENTS

CN        201453837 U    5/2010
WO    WO-2006029257 A2    3/2006
(Continued)

OTHER PUBLICATIONS

Kothandaraman, Sridhar, et al., "System and Method for Connecting Devices to a Neurostimulator", U.S. Appl. No. 61/694,695, filed Aug. 29, 2012.
(Continued)

*Primary Examiner* — Nicole F Johnson
(74) *Attorney, Agent, or Firm* — Schwegman Lundberg & Woessner, P.A.

(57) ABSTRACT

A method of operating an implantable neuromodulator includes calculating an index for each of a plurality of modulation parameter sets, wherein each modulation parameter set includes a respective plurality of modulation parameters from which the respective index is calculated, serially conveying electrical modulation energy to a patient in accordance with each of the plurality of modulation parameter sets, causing the patient to perceive paresthesia in response to the conveyance of the electrical modulation energy to the tissue in accordance with one of the plurality of modulation parameter sets, identifying the calculated index for that one modulation parameter set as a perception threshold index based on the perceived paresthesia, and storing the identified perception threshold index. The method may also include determining a new modulation parameter set based on the identified perception threshold index, and conveying electrical modulation energy to the tissue in accordance with the new modulation parameter set.

18 Claims, 16 Drawing Sheets

(51) Int. Cl.
*A61N 1/05* (2006.01)
*A61N 1/372* (2006.01)

(56) References Cited

U.S. PATENT DOCUMENTS

| | | | |
|---|---|---|---|
| 6,516,227 B1 | 2/2003 | Meadows et al. | |
| 6,675,046 B2 | 1/2004 | Holsheimer | |
| 6,731,986 B2 * | 5/2004 | Mann | A61N 1/36164 607/30 |
| 6,895,280 B2 | 5/2005 | Meadows et al. | |
| 6,993,384 B2 | 1/2006 | Bradley et al. | |
| 7,317,948 B1 | 1/2008 | King et al. | |
| 7,333,857 B2 | 2/2008 | Campbell | |
| 7,539,538 B2 | 5/2009 | Parramon et al. | |
| 7,627,384 B2 | 12/2009 | Ayal et al. | |
| 7,650,184 B2 | 1/2010 | Walter | |
| 7,979,133 B2 | 7/2011 | Feler et al. | |
| 7,987,000 B2 | 7/2011 | Moffitt et al. | |
| 8,019,439 B2 | 9/2011 | Kuzma et al. | |
| 8,160,328 B2 | 4/2012 | Goetz et al. | |
| 8,180,129 B2 | 5/2012 | Goetz et al. | |
| 8,224,453 B2 | 7/2012 | De Ridder | |
| 8,255,057 B2 | 8/2012 | Fang et al. | |
| 8,332,039 B1 | 12/2012 | Huynh et al. | |
| 8,355,797 B2 | 1/2013 | Caparso et al. | |
| 8,412,345 B2 | 4/2013 | Moffitt | |
| 8,437,857 B2 | 5/2013 | Moffitt et al. | |
| 8,455,716 B2 | 6/2013 | Huang et al. | |
| 8,504,147 B2 | 8/2013 | Deem et al. | |
| 8,615,300 B2 | 12/2013 | Feler et al. | |
| 8,649,874 B2 | 2/2014 | Alataris et al. | |
| 8,660,653 B2 | 2/2014 | Kothandaraman | |
| 8,670,831 B2 | 3/2014 | Wacnik et al. | |
| 8,676,329 B2 | 3/2014 | Wacnik et al. | |
| 8,676,331 B2 | 3/2014 | Parker | |
| 8,700,178 B2 | 4/2014 | Anderson | |
| 8,731,675 B2 | 5/2014 | Ranu et al. | |
| 8,751,009 B2 | 6/2014 | Wacnik | |
| 2003/0032992 A1 | 2/2003 | Thacker et al. | |
| 2003/0139781 A1 | 7/2003 | Bradley et al. | |
| 2004/0116978 A1 | 6/2004 | Bradley | |
| 2005/0245987 A1 | 11/2005 | Woods et al. | |
| 2007/0150036 A1 | 6/2007 | Anderson | |
| 2008/0188909 A1 | 8/2008 | Bradley | |
| 2008/0215119 A1 | 9/2008 | Woods et al. | |
| 2009/0196472 A1 | 8/2009 | Goetz et al. | |
| 2009/0198306 A1 | 8/2009 | Goetz et al. | |
| 2009/0204173 A1 | 8/2009 | Fang et al. | |
| 2010/0010566 A1 | 1/2010 | Thacker et al. | |
| 2010/0121409 A1 | 5/2010 | Kothandaraman et al. | |
| 2010/0274312 A1 | 10/2010 | Alataris et al. | |
| 2010/0274314 A1 | 10/2010 | Alataris et al. | |
| 2010/0274315 A1 | 10/2010 | Alataris et al. | |
| 2010/0274317 A1 | 10/2010 | Parker et al. | |
| 2010/0274318 A1 | 10/2010 | Walker et al. | |
| 2010/0274326 A1 | 10/2010 | Chitre et al. | |
| 2011/0282414 A1 | 11/2011 | Kothandaraman et al. | |
| 2012/0059446 A1 | 3/2012 | Wallace et al. | |
| 2012/0083709 A1 | 4/2012 | Parker et al. | |
| 2012/0253422 A1 | 10/2012 | Thacker et al. | |
| 2012/0265279 A1 | 10/2012 | Zhu | |
| 2012/0283797 A1 | 11/2012 | De Ridder | |
| 2012/0290041 A1 | 11/2012 | Kim et al. | |
| 2013/0066411 A1 | 3/2013 | Thacker et al. | |
| 2013/0116752 A1 | 5/2013 | Parker et al. | |
| 2013/0268021 A1 | 10/2013 | Moffitt | |
| 2013/0296975 A1 | 11/2013 | Lee et al. | |
| 2014/0081349 A1 | 3/2014 | Lee et al. | |
| 2014/0277267 A1 | 9/2014 | Vansickle et al. | |

FOREIGN PATENT DOCUMENTS

| | | | |
|---|---|---|---|
| WO | WO-2006135791 A2 | 12/2006 | |
| WO | WO-2015089411 A2 | 6/2015 | |
| WO | WO-2015089411 A3 | 6/2015 | |

OTHER PUBLICATIONS

Lee, Dongchul, "Neurostimulation System for Defining a Generalized Ideal Multipole Configuration", U.S. Appl. No. 61/452,965, filed Mar. 15, 2011.

Rao, Prakash, et al., "Technique for Linking Electrodes Together During Programming of Neurostimulation System", U.S. Appl. No. 61/561,760, filed Nov. 18, 2011.

Vansickle, Dennis Allen, et al., "Neuromodulation System and Method for Transitioning Between Programming Modes", U.S. Appl. No. 14/214,752, filed Mar. 15, 2014.

Vansickle, Dennis Allen, "Systems and Methods for Delivering Sub-Threshold Therapy to a Patient", U.S. Appl. No. 61/801,917, filed Mar. 15, 2013.

Warman, Eduardo N., et al., "Modeling the Effects of Electric Fields on Nerve Fibers: Determination of Excitation Thresholds", IEEE Transactions on Biomedical Engineering, vol. 39, No. 12, Dec. 1992, (Dec. 1992).

Zhu, Changfang, et al., "Neurostimulation System for Estimating Desired Stimulation Amplitude for Electrode Configuration", U.S. Appl. No. 61/427,027, filed Dec. 23, 2010.

Zhu, Changfang, et al., "Neurostimulation System for Implementing Model-Based Estimate of Neurostimulation Effects", U.S. Appl. No. 61/427,059, filed Dec. 23, 2010.

"International Application Serial No. PCT/US2014/070046, International Search Report mailed Jul. 24, 2015", 6 pgs.

"International Application Serial No. PCT/US2014/070046, Invitation to Pay Add'l Fees and Partial Search Report mailed Apr. 13, 2015", 5 pgs.

"International Application Serial No. PCT/US2014/070046, Written Opinion mailed Jul. 24, 2015", 6 pgs.

* cited by examiner

SYSTEMS AND METHODS FOR PROGRAMMING A NEUROMODULATION SYSTEM

CLAIM OF PRIORITY

This application claims the benefit of priority under 35 U.S.C. §119(e) of U.S. Provisional Patent Application Ser. No. 61/915,422, filed on Dec. 12, 2013, which is herein incorporated by reference in its entirety.

FIELD OF THE INVENTION

The present inventions relate to tissue modulation systems, and more particularly, to programmable neuromodulation systems.

BACKGROUND OF THE INVENTION

Implantable neuromodulation systems have proven therapeutic in a wide variety of diseases and disorders. Pacemakers and Implantable Cardiac defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations, Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems, such as the Freehand system by NeuroControl (Cleveland, Ohio), have been applied to restore some functionality to paralyzed extremities in spinal cord injury patients.

These implantable neuromodulation systems typically include one or more electrodes carrying stimulation leads, which are implanted at the desired stimulation site, and an implantable neuromodulation device (e.g., an implantable pulse generator (IPG)) implanted remotely from the stimulation sire, but coupled either directly to the neuromodulation lead(s) or indirectly to the neuromodulation lead(s) via a lead extension. The neuromodulation system may further comprise a handheld external control device (e.g., a remote control (RC)) to remotely instruct the neuromodulator to generate electrical stimulation pulses in accordance with selected modulation parameters.

Implantable neuromodulation devices are active devices requiring energy for operation, and thus, the neuromodulation system oftentimes includes an external charger to recharge a neuromodulation device, so that a surgical procedure to replace a power depleted neuromodulation device can be avoided. To wirelessly convey energy between the external charger and the implanted neuromodulation device, the charger typically includes an alternating current (AC) charging coil that supplies energy to a similar charging coil located in or on the neuromodulation device. The energy received by the charging coil located on the neuromodulation device can then be stored in a rechargeable battery within the neuromodulation device, which can then be used to power the electronic componentry on-demand. Depending on the settings, the neuromodulation device may need to be recharged every 1-30 days.

Electrical stimulation energy may be delivered from the neuromodulation device to the electrodes in the form of an electrical pulsed waveform. Thus, stimulation energy may be controllably delivered to the electrodes to stimulate neural tissue. The configuration of electrodes used to deliver electrical pulses to the targeted tissue constitutes an electrode configuration, with the electrodes capable of being selectively programmed to act as anodes (positive), cathodes (negative), or left off (zero). In other words, an electrode configuration represents the polarity being positive, negative, or zero. Other parameters that may be controlled or varied include the amplitude, pulse width, and rate (or frequency) of the electrical pulses provided through the electrode array. Each electrode configuration, along with the electrical pulse parameters, can be referred to as a "modulation parameter set."

The lead or leads are typically placed in a location, such that the electrical stimulation will cause paresthesia. The current understanding is that paresthesia induced by the stimulation and perceived by the patient should be located in approximately the same place in the patient's body as the pain that is the target of treatment. If a lead is not correctly positioned, it is possible that the patient will receive little or no benefit from an implanted SCS system. Thus, correct lead placement can mean the difference between effective and ineffective pain therapy. When electrical leads are implanted within the patient, the computerized programming system, in the context of an operating room (OR) mapping procedure, may be used to instruct the neuromodulation device to apply electrical stimulation to test placement of the leads and/or electrodes, thereby assuring that the leads and/or electrodes are implanted in effective locations within the patient.

Although alternative or artifactual sensations are usually appreciated by patients, patients sometimes report these sensations to be uncomfortable, and therefore, they can be considered an adverse side-effect to neuromodulation therapy in some cases. It has been shown that the delivery of sub-threshold electrical energy (e.g., high-rate pulsed electrical energy and/or low pulse width electrical energy) can be effective in providing neuromodulation therapy for chronic pain without causing paresthesia.

Once the leads are correctly positioned, a fitting procedure, which may be referred to as a navigation session, may be performed using the computerized programming system to program the external control device, and if applicable the neuromodulation device, with a set of modulation parameters that best addresses the painful site. Thus, the navigation session may be used to pinpoint the volume of activation (VOA) or areas correlating to the pain. Such programming ability is particularly advantageous for targeting the tissue during implantation, or after implantation should the leads gradually or unexpectedly move that would otherwise relocate the stimulation energy away from the target site. By reprogramming the neuromodulation device (typically by independently varying the stimulation energy on the electrodes), the volume of activation (VOA) can often be moved back to the effective pain site without having to re-operate on the patient in order to reposition the lead and its electrode array. When adjusting the volume of activation (VOA) relative to the tissue, it is desirable to make small changes in the proportions of current, so that changes in the spatial recruitment of nerve fibers will be perceived by the patient as being smooth and continuous and to have incremental targeting capability.

An external control device can be used to instruct the neuromodulation device to generate electrical stimulation pulses in accordance with the selected modulation parameters. Typically, the modulation parameters programmed into the neuromodulation device can be adjusted by manipulating controls on the external control device to modify the electrical stimulation provided by the neuromodulation device system to the patient. Thus, in accordance with the modulation parameters programmed by the external control device, electrical pulses can be delivered from the neuromodulation device to the stimulation electrode(s) to stimulate or activate a volume of tissue in accordance with a set of modulation parameters and provide the desired efficacious therapy to the patient. The best modulation parameter set will typically be one that delivers stimulation energy to the volume of tissue that must be stimulated in order to provide the therapeutic benefit (e.g., treatment of pain), while minimizing the volume of non-target tissue that is stimulated.

The clinician generally programs the neuromodulation device through a computerized programming system. This programming system can be a self-contained hardware/software system, or can be defined predominantly by software running on a standard personal computer (PC). The PC or custom hardware may actively control the characteristics of the electrical stimulation generated by the neuromodulation device to allow the optimum modulation parameters to be determined based on patient feedback or other means and to subsequently program the neuromodulation device with the optimum modulation parameter set or sets. The computerized programming system may be operated by a clinician attending the patient in several scenarios.

One known computerized programming system for SCS is called the Bionic Navigator®, available from Boston Scientific Neuromodulation Corporation. The Bionic Navigator® is a software package that operates on a suitable PC and allows clinicians to program modulation parameters into an external handheld programmer (referred to as a remote control). Each set of modulation parameters, including fractionalized current distribution to the electrodes (as percentage cathodic current, percentage anodic current, or off), may be stored in both the Bionic Navigator® and the remote control and combined into a stimulation program that can then be used to stimulate multiple regions within the patient.

Current computerized programming systems display the absolute value of electrical pulse parameters and enable the clinician and the patient to program the neuromodulation device by altering these absolute values of electrical pulse parameters either manually or by steering a virtual locus. However, such systems and programming user interfaces do not enable more intuitive programming. For instance, such systems and interfaces do not provide information about the perception threshold (i.e., the modulation signal level above which a patient feels paresthesia). Accordingly, these exists a need for computerized programming systems and methods that provide information about a patient's perception threshold and facilitates programming and modifying modulation parameter sets and their resulting stimulation programs using information about the perception threshold.

As discussed above, lead migration after implantation and programming can relocate the stimulation energy away from the target site. Consequently lead migration can require reprogramming of the neuromodulation device by independently varying the stimulation energy on the electrodes to move the VOA back to the effective pain site. Independently adjusting stimulation energy for an entire array of electrodes across a series of stimulation programs can be time-consuming and error-prone. There, thus, exists a need for an automatic or semi-automatic method of simultaneously adjusting the modulation parameter sets of a series of stimulation programs.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

SUMMARY OF THE INVENTION

Figure 1:
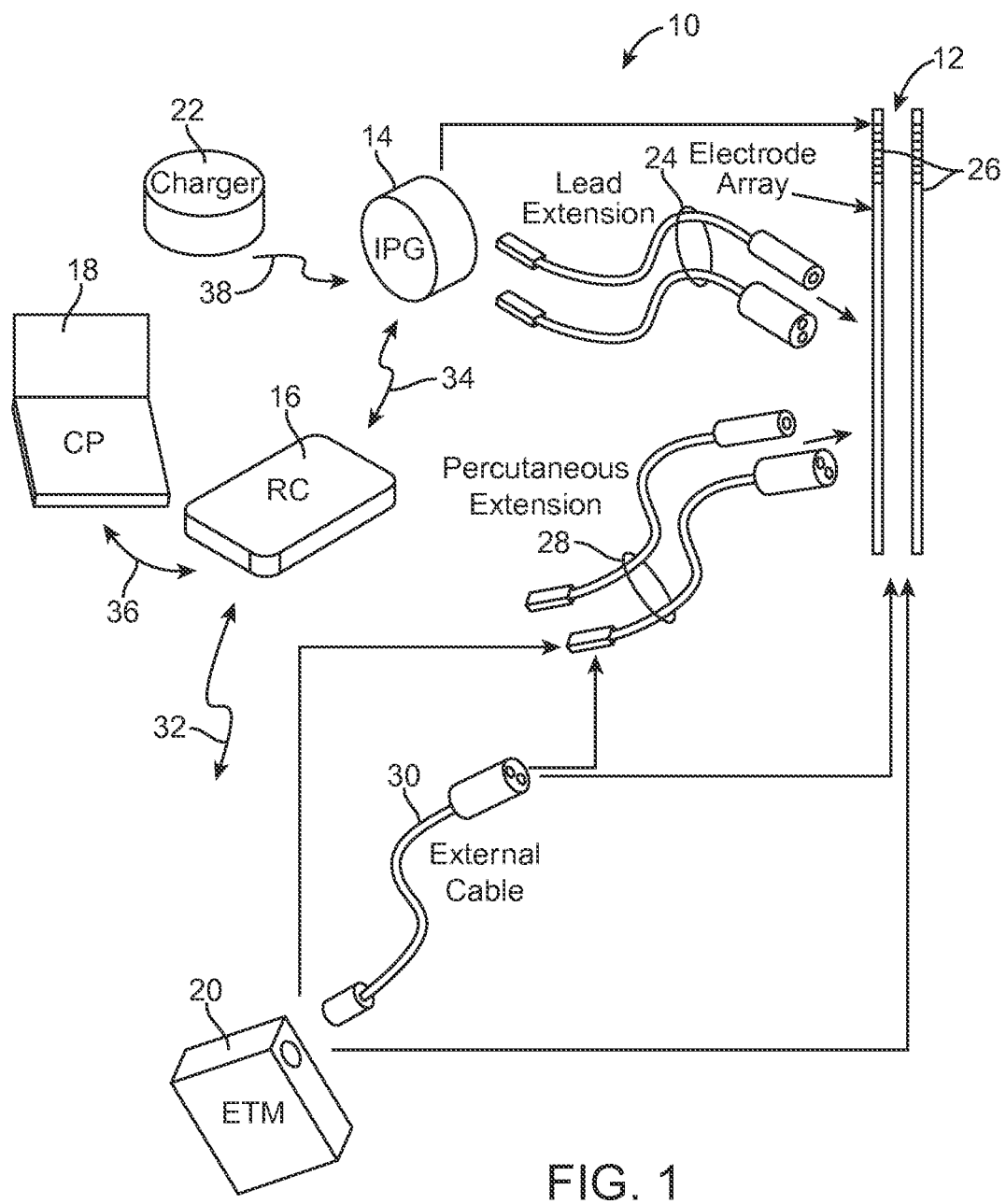
FIG. 1 is a plan view of a Spinal Cord Modulation (SCM) system constructed in accordance with one embodiment of the present inventions.

In accordance with a first aspect of the present inventions, a method of operating an implantable neuromodulator coupled to an electrode array implanted adjacent tissue of a patient having a medical condition is provided. The method comprises calculating an index for each of a plurality of modulation parameter sets, wherein each modulation parameter set includes a respective plurality of modulation parameters from which the respective index is calculated. The method also comprises serially conveying electrical modulation energy to the tissue in accordance with each of the plurality of modulation parameter sets. The method further comprises causing the patient to perceive paresthesia in response to the conveyance of the electrical modulation energy to the tissue in accordance with one of the plurality of modulation parameter sets. Moreover, the method comprises identifying the calculated index for the one of the plurality of modulation parameter sets as a perception threshold index based on the perceived paresthesia. In addition, the method comprises storing the identified perception threshold index.

In one embodiment, the method also comprises determining a new modulation parameter set based on the identified perception threshold index, and conveying electrical modulation energy to the tissue in accordance with the new modulation parameter set. Determining a new modulation parameter set based on the identified perception threshold index may comprise selecting a new index by applying a function to the identified perception index, and determining a plurality of modulation parameters based on the new index.

In another embodiment, the method also comprises modifying a modulation parameter set based on the identified perception threshold index, and conveying electrical modulation energy to the tissue in accordance with the modified modulation parameter set. Modifying a modulation parameter set based on the identified perception threshold index may comprise selecting a new index by applying a function to the identified perception index, and determining a plurality of modulation parameters based on the new index.

In one or more embodiments, the new index may be a percentage of the identified perception threshold index. The method may also comprise establishing lower and upper limits for the new index based on respective minimum and maximum percentages of the identified perception threshold index. Conveying electrical modulation energy to the tissue in accordance with the new modulation parameter set may comprise conveying sub-threshold or super-threshold electrical modulation energy. The modulation parameters may be selected from the group consisting of amplitude, pulse width, duty cycle, frequency, lead location, electrical field locus, electrical field focus, and electrical field center point size. Each of the plurality of modulation parameter sets may differ from each of the other modulation parameters sets in more than one modulation parameter. The index may be an energy index calculated by multiplying respective an amplitude, a pulse width, and a frequency.

In still another embodiment, each of the plurality of modulation parameter sets directs the implantable neuromodulator to convey electrical modulation energy at a first axial level, the method further comprising identifying another perception threshold index for electrical modulation energy conveyed at a second axial level. In yet another embodiment, each of the plurality of modulation parameter sets directs the implantable neuromodulator to convey electrical modulation energy through a first electrode, the method further comprising identifying another perception threshold index for electrical modulation energy conveyed through a second electrode.

In another embodiment, the method also comprises graphically displaying the identified perception threshold index. The method may also comprise graphically displaying an index of a modulation parameter set as a function of the identified perception threshold index. The method may further comprise graphically differentiating indices for modulation parameter sets configured to direct conveyance of sub-threshold from indices for modulation parameter sets configured to direct conveyance of super-threshold modulation energy. In addition, the method may comprise graphically displaying a discomfort index of another modulation parameter set corresponding to stimulation causing discomfort to the patient.

In yet another embodiment, the method also comprises causing the patient to perceive paresthesia in response to the conveyance of the electrical modulation energy to the tissue in accordance with more than one of the plurality of modulation parameter sets, and identifying the lowest calculated index for the more than one of the plurality of modulation parameter sets as the perception threshold index based on the perceived paresthesia.

In accordance with a second aspect of the present inventions, a method of modifying a modulation parameter set is provided. The method comprises calculating a first index for a first plurality of modulation parameters, wherein the first plurality of modulation parameters are part of a first stimulation program. The method also comprises calculating a first normalized value for the first index as a percentage of a first perception threshold index. The method further comprises identifying a second perception threshold index. Moreover, the method comprises calculating a second index from the identified second perception index and the normalized value. In addition, the method comprises determining a second plurality of modulation parameters from the calculated second index. Additionally, the method comprises modifying at least one of the first plurality of modulation parameters to result in the second plurality of modulation parameters and a second stimulation program.

In one embodiment, the method also comprises calculating a third index for a third plurality of modulation parameters, wherein the third plurality of modulation parameters are part of a third stimulation program. The method further comprises calculating a second normalized value for the third index as a percentage of the first perception threshold index. Moreover, the method comprises calculating a fourth index from the identified second perception index and the second normalized value. In addition, the method comprises determining a fourth plurality of modulation parameters from the calculated fourth index. Additionally, the method comprises modifying at least one of the third plurality of modulation parameters to result in the fourth plurality of modulation parameters and a fourth stimulation program. Modifying at least one of the first plurality of modulation parameters and modifying at least one of the third plurality of modulation parameters may be performed simultaneously.

In one or more embodiments, modifying at least one of the first plurality of modulation parameters is performed automatically or manually. The method may also comprise modifying the absolute value of the at least one of the first plurality of modulation parameters. The first and second indices may be energy indices calculated by multiplying respective amplitudes, pulse widths, and frequencies.

In accordance with a third aspect of the present inventions, a method of simultaneously modifying a plurality of modulation parameter sets is provided. The method comprises calculating a first plurality of indices from respective ones of a first plurality of modulation parameter sets, wherein each of the first plurality of modulation parameter sets is a part of respective ones of a first plurality of stimulation programs. The method also comprises calculating a plurality of normalized values for respective ones of the calculated indices as a percentage of a first perception threshold index. The method further comprises identifying a second perception threshold index. Moreover, the method comprises calculating a second plurality of indices from the identified second perception index and respective ones of the plurality of normalized values. In addition, the method comprises determining a second plurality of modulation parameter sets from the calculated second plurality of indices. Additionally, the method comprises simultaneously modifying the plurality of modulation parameter sets to result in the second plurality of modulation parameter sets and a second plurality of stimulation programs. The simultaneously modifying the plurality of modulation parameter sets may be performed automatically. Each of the first and second pluralities of indices may be an energy index calculated by multiplying respective amplitudes, pulse widths, and frequencies.

Other and further aspects and features of the invention will be evident from reading the following detailed description of the preferred embodiments, which are intended to illustrate, not limit, the invention.

DETAILED DESCRIPTION OF THE EMBODIMENTS

Turning first to FIG. 1, an exemplary SCM system 10 generally includes a plurality (in this case, two) of implantable neuromodulation leads 12, an implantable pulse generator (IPG) 14, an external remote controller RC 16, a clinician's programmer (CP) 18, an external trial modulator (ETM) 20, and an external charger 22.

The IPG 14 is physically connected via one or more percutaneous lead extensions 24 to the neuromodulation leads 12, which carry a plurality of electrodes 26 arranged in an array. In the illustrated embodiment, the neuromodulation leads 12 are percutaneous leads, and to this end, the electrodes 26 are arranged in-line along the neuromodulation leads 12. The number of neuromodulation leads 12 illustrated is two, although any suitable number of neuromodulation leads 12 can be provided, including only one, as long as the number of electrodes 26 is greater than two (including the IPG case) to allow for lateral steering of the current. Alternatively, a surgical paddle lead can be used in place of one or more of the percutaneous leads. As will be described in further detail below, the IPG 14 includes pulse generation circuitry that delivers electrical modulation energy in the form of a pulsed electrical waveform (i.e., a temporal series of electrical pulses) to the electrode array 26 in accordance with a set of modulation parameters.

The ETM 20 may also be physically connected via the percutaneous lead extensions 28 and external cable 30 to the neuromodulation leads 12. The ETM 20, which has similar pulse generation circuitry as the IPG 14, also delivers electrical modulation energy in the form of a pulse electrical waveform to the electrode array 26 accordance with a set of modulation parameters. The major difference between the ETM 20 and the IPG 14 is that the ETM 20 is a non-implantable device that is used on a trial basis after the neuromodulation leads 12 have been implanted and prior to implantation of the IPG 14, to test the responsiveness of the modulation that is to be provided. Thus, any functions described herein with respect to the IPG 14 can likewise be performed with respect to the ETM 20. For purposes of brevity, the details of the ETM 20 will not be described herein. Details of exemplary embodiments of ETM are disclosed in U.S. Pat. No. 6,895,280, which is expressly incorporated herein by reference.

The RC 16 may be used to telemetrically control the ETM 20 via a bi-directional RF communications link 32. Once the IPG 14 and neuromodulation leads 12 are implanted, the RC 16 may be used to tele metrically control the IPG 14 via a bi-directional RF communications link 34. Such control allows the IPG 14 to be turned on or off and to be programmed with different modulation parameter sets. The IPG 14 may also be operated to modify the programmed modulation parameters to actively control the characteristics of the electrical modulation energy output by the IPG 14. As will be described in further detail below, the CP 18 provides clinician detailed modulation parameters for programming the IPG 14 and ETM 20 in the operating room and in follow-up sessions.

The CP 18 may perform this function by indirectly communicating with the IPG 14 or ETM 20, through the RC 16, via an IR communications link 36. Alternatively, the CP 18 may directly communicate with the IPG 14 or ETM 20 via an RF communications link (not shown). The clinician detailed modulation parameters provided by the CP 18 are also used to program the RC 16, so that the modulation parameters can be subsequently modified by operation of the RC 16 in a stand-alone mode (i.e., without the assistance of the CP 18).

The external charger 22 is a portable device used to transcutaneously charge the IPG 14 via an inductive link 38. Once the IPG 14 has been programmed, and its power source has been charged by the external charger 22 or otherwise replenished, the IPG 14 may function as programmed without the RC 16 or CP 18 being present. For purposes of brevity, the details of the external charger 22 will not be described herein. Details of exemplary embodiments of the external charger are disclosed in U.S. Pat. No. 6,895,280, which is expressly incorporated herein by reference.

Figure 2:
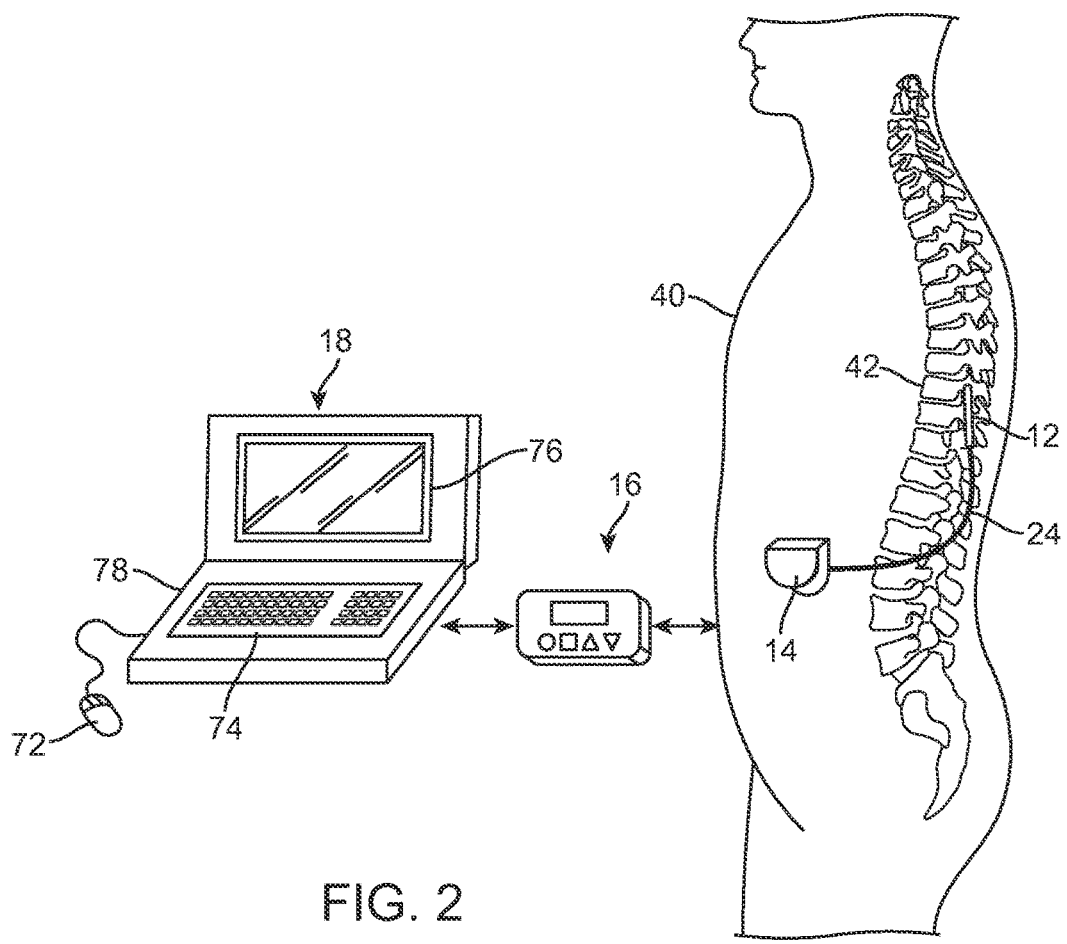
FIG. 2 is a plan view of the SCM system of FIG. 1 in use with a patient.

As shown in FIG. 2, the neuromodulation leads 12 are implanted within the spinal column 42 of a patient 40. The preferred placement of the neuromodulation leads 12 is adjacent, i.e., resting upon, the spinal cord area to be stimulated. Due to the lack of space near the location where the neuromodulation leads 12 exit the spinal column 42, the IPG 14 is generally implanted in a surgically-made pocket either in the abdomen or above the buttocks. The IPG 14 may, of course, also be implanted in other locations of the patient's body. The lead extension 24 facilitates locating the IPG 14 away from the exit point of the neuromodulation leads 12. As shown in FIG. 2, the CP 18 communicates with the IPG 14 via the RC 16.

Figure 3:
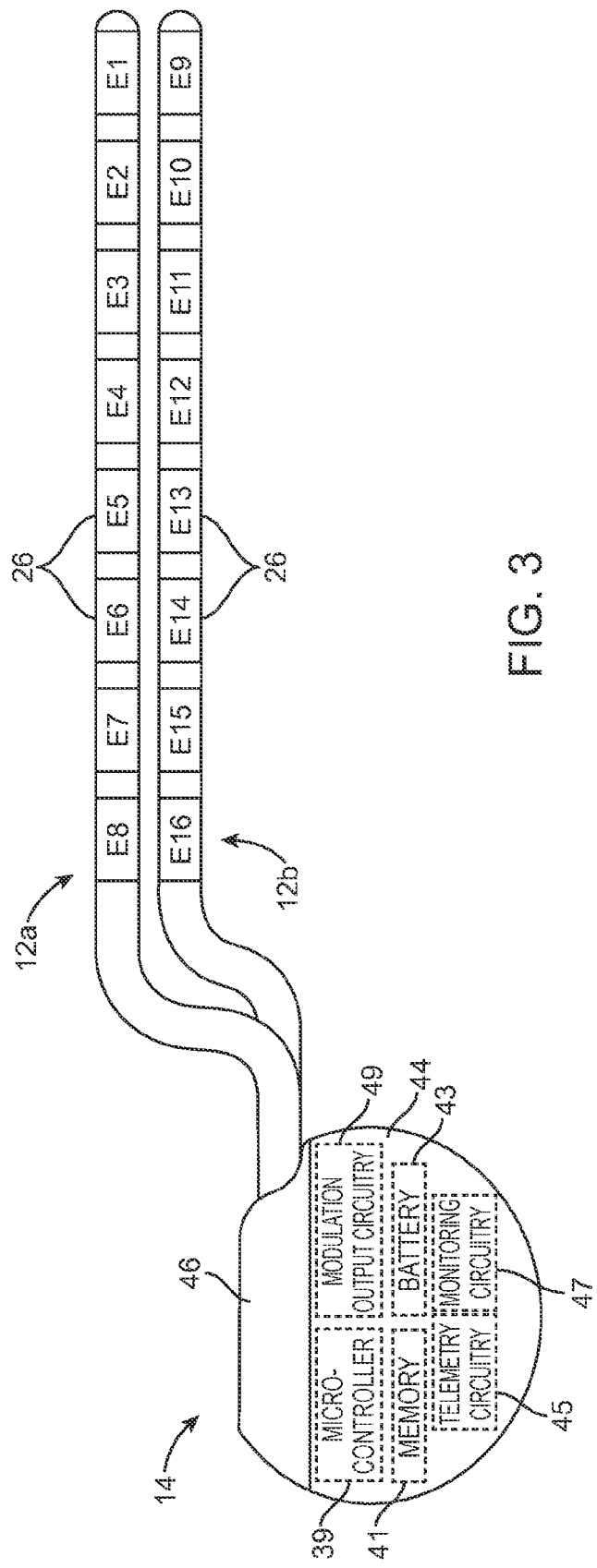
FIG. 3 is a profile view of an implantable pulse generator (IPG) and percutaneous leads used in the SCM system of Hg. 1.

Referring now to FIG. 3, the external features of the neuromodulation leads 12 and the IPG 14 will be briefly described. One of the neuromodulation leads 12a has eight electrodes 26 (labeled E1-E8), and the other neuromodulation lead 12b has eight electrodes 26 (labeled E9-E16). The actual number and shape of leads and electrodes will, of course, vary according to the intended application. The IPG 14 comprises an outer case 44 for housing the electronic and other components (described in further detail below), and a connector 46 to which the proximal ends of the neuromodulation leads 12 mates in a manner that electrically couples the electrodes 26 to the electronics within the outer case 44. The outer case 44 is composed of an electrically conductive, biocompatible material, such as titanium, and forms a hermetically sealed compartment wherein the internal electronics are protected from the body tissue and fluids. In some cases, the outer case 44 may serve as an electrode.

The IPG 14 comprises electronic components, such as a controller/processor (e.g., a microcontroller) 39, memory 41, a battery 43, telemetry circuitry 45, monitoring circuitry 47, modulation output circuitry 49, and other suitable components known to those skilled in the art. The microcontroller 39 executes a suitable program stored in memory 41, for directing and controlling the neuromodulation performed by IPG 14. Telemetry circuitry 45, including an antenna (not shown), is configured for receiving programming data (e.g., the operating program and/or modulation parameters) from the RC 16 and/or CP 18 in an appropriate modulated carrier signal, which the programming data is then stored in the memory (not shown). The telemetry circuitry 45 is also configured for transmitting status data to the RC 16 and/or CP 18 in an appropriate modulated carrier signal. The battery 43, which may be a rechargeable lithium-ion or lithium-ion polymer battery, provides operating power to IPG 14. The monitoring circuitry 47 is configured for monitoring the present capacity level of the battery 43.

The modulation output circuitry 49 provides electrical modulation energy in the form of a pulsed electrical waveform to the electrodes 26 in accordance with a set of modulation parameters programmed into the IPG 14. Such modulation parameters may comprise electrode combinations, which define the electrodes that are activated as anodes (positive), cathodes (negative), and turned of (zero), percentage of modulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse width (measured in microseconds), pulse rate (measured in pulses per second), and burst rate (measured as the modulation on duration X and modulation off duration Y).

Electrical modulation will occur between a plurality of activated electrodes, one of which may be the IPG case 44. Modulation energy may be transmitted to the tissue in a monopolar or multipolar (e.g., bipolar, tripolar, etc.) fashion. Monopolar modulation occurs when a selected one of the lead electrodes 26 is activated along with the case of the IPG 14, so that modulation energy is transmitted between the selected electrode 26 and case. Bipolar modulation occurs when two of the lead electrodes 26 are activated as anode and cathode, so that modulation energy is transmitted between the selected electrodes 26. For example, electrode E3 on the first lead 12*a* may be activated as an anode at the same time that electrode E11 on the second lead 12*b* is activated as a cathode. Tripolar modulation occurs when three of the lead electrodes 26 are activated, two as anodes and the remaining one as a cathode, or two as cathodes and the remaining one as an anode. For example, electrodes E4 and E5 on the first lead 12*a* may be activated as anodes at the same time that electrode E12 on the second lead 12*b* is activated as a cathode. Such multipolar modulation facilitates lateral steering and fractionalization of current.

Any of the electrodes E1-E16 and case electrode may be assigned to up to k possible groups or timing "channels." In one embodiment, k may equal four. The timing channel identifies which electrodes are selected to synchronously source or sink current to create an electric field in the tissue to be stimulated. Amplitudes and polarities of electrodes on a channel may vary. In particular, the electrodes can be selected to be positive (sourcing current), negative (sinking current), or off (no current) polarity in any of the k timing channels.

In the illustrated embodiment, IPG 14 can individually control the magnitude of electrical current flowing through each of the electrodes. In this case, it is preferred to have a current generator, wherein individual current-regulated amplitudes from independent current sources for each electrode may be selectively generated. Although this system is optimal to take advantage of the invention, other neuromodulators that may be used with the invention include neuromodulators having voltage regulated outputs. While individually programmable electrode amplitudes are optimal to achieve fine control, a single output source switched across electrodes may also be used, although with less fine control in programming. Mixed current and voltage regulated devices may also be used with the invention. Further details discussing the detailed structure and function of IPGs are described more fully in U.S. Pat. Nos. 6,516,227 and 6,993,384, which are expressly incorporated herein by reference.

It should be noted that rather than an IPG, the SCM system 10 may alternatively utilize an implantable receiver-stimulator (not shown) connected to the neuromodulation leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-modulator. The implanted receiver-modulator receives the signal and generates the modulation in accordance with the control signals.

The IPG 14 may be operated in one of a super-threshold delivery mode, a sub-threshold delivery mode, and a hybrid delivery mode. While in the super-threshold delivery mode, the IPG 14 is configured for delivering electrical modulation energy that provides super-threshold therapy to the patient (in this case, causes the patient to perceive paresthesia). While in the sub-threshold delivery mode, the IPG 14 is configured for delivering electrical modulation energy that provides sub-threshold therapy to the patient (in this case, does not cause the patient to perceive paresthesia). While in the hybrid delivery mode, the IPG 14 is configured for delivered electrical modulation energy that simultaneously provides both super-threshold therapy and sub-threshold therapy to the patient. Further details discussing modulation phases and delivery modes are described more fully in U.S. Provisional Patent Application Ser. No. 61/801,917, entitled "Systems and Methods for Delivering Sub-Threshold Therapy to a Patient," which is expressly incorporated herein by reference.

Figure 4:
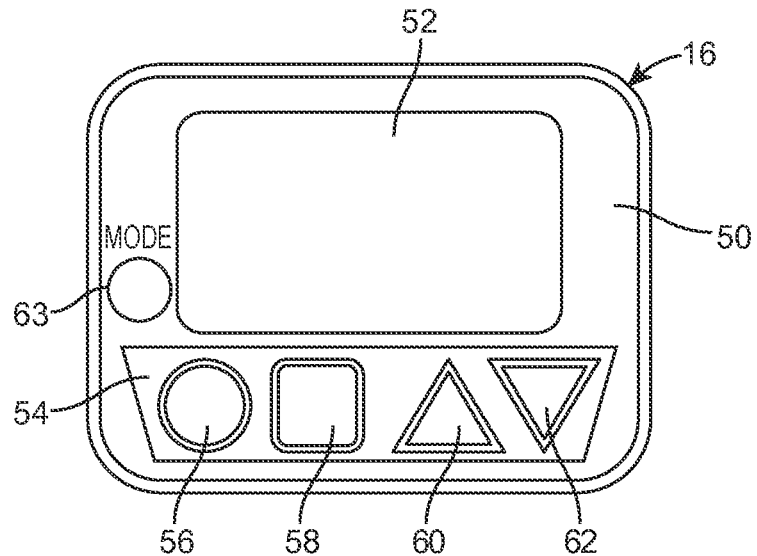
FIG. 4 is front view of a remote control (RC) used in the SCM system of FIG. 1.

Referring now to FIG. 4, one exemplary embodiment of an RC 16 will now be described. As previously discussed, the RC 16 is capable of communicating with the IPG 14, CP 18, or ETM 20. The RC 16 comprises a casing 50, which houses internal componentry (including a printed circuit board (PCB)), and a lighted display screen 52 and button pad 54 carried by the exterior of the casing 50. In the illustrated embodiment, the display screen 52 is a lighted flat panel display screen, and the button pad 54 comprises a membrane switch with metal domes positioned over a flex circuit, and a keypad connector connected directly to a PCB. In an optional embodiment, the display screen 52 has touchscreen capabilities. The button pad 54 includes a multitude of buttons 56, 58, 60, and 62, which allow the IPG 14 to be turned ON and OFF, provide for the adjustment or setting of modulation parameters within the IPG 14, and provide for selection between screens.

In the illustrated embodiment, the button 56 serves as an ON/OFF button that can be actuated to turn the IPG 14 ON and OFF. The button 58 serves as a select button that can be actuated to switch the RC 16 between screen displays and/or parameters. The buttons 60 and 62 serve as up/down buttons that can be actuated to increment or decrement any of modulation parameters of the pulsed electrical train generated by the IPG 14, including pulse amplitude, pulse width, and pulse rate. For example, the selection button 58 can be actuated to place the RC 16 in a "Pulse Amplitude Adjustment Mode," during which the pulse amplitude can be adjusted via the up/down buttons 60, 62, a "Pulse Width Adjustment Mode," during which the pulse width can be adjusted via the up/down buttons 60, 62, and a "Pulse Rate Adjustment Mode," during which the pulse rate can be adjusted via the up/down buttons 60, 62. The selection button 58 can also be actuated to place the RC 16 is a "Program Generation Mode" and a "Program Modification Mode," as described in greater detail below. During these two modes, a modulation signal index (described below) of a modulation parameter set can be adjusted via the up/down buttons 60, 62. Alternatively, dedicated up/down buttons can be provided for each modulation parameter and the modulation signal index. Rather than using up/down buttons, any other type of actuator, such as a dial, slider bar, or keypad, can be used to increment or decrement the modulation parameters.

Figure 5:
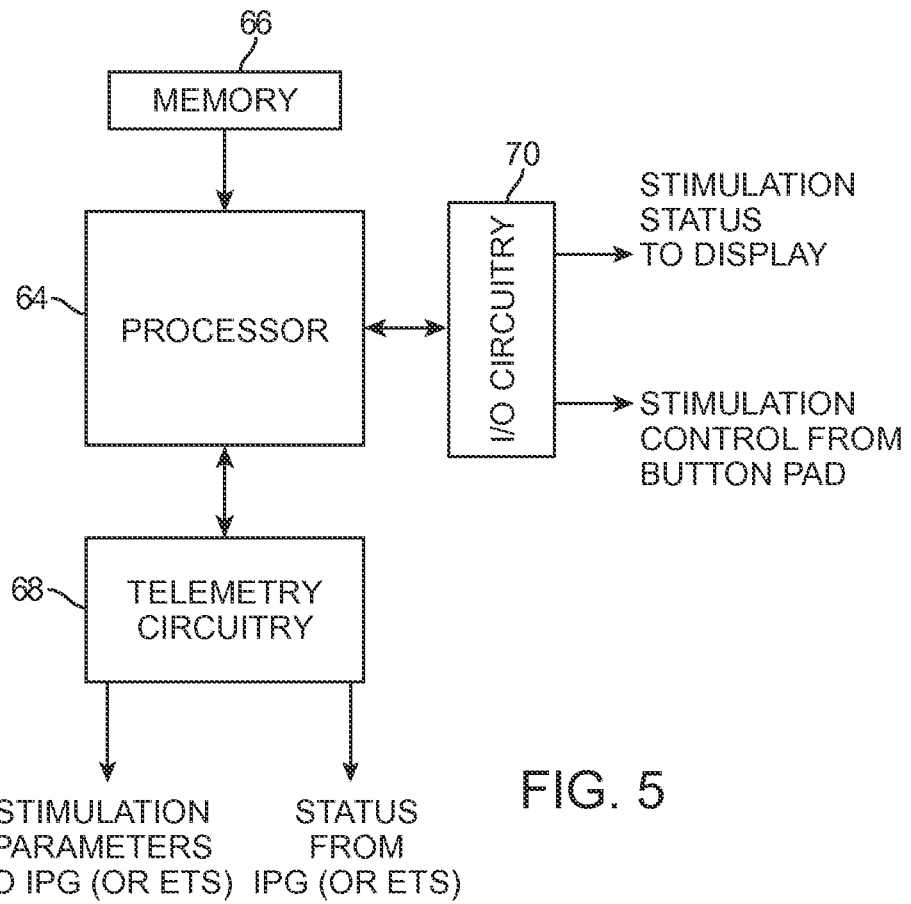
FIG. 5 is a block diagram of the internal components of the RC of FIG. 4.

Referring to FIG. 5, the internal components of an exemplary RC 16 will now be described. The RC 16 generally includes a controller/processor 64 (e.g., a microcontroller); memory 66 that stores an operating program for execution by the controller/processor 64, as well as modulation parameter sets; input/output circuitry, and in particular, telemetry circuitry 68 for outputting modulation parameters to the IPG 14 or otherwise directing the IPG 14 to deliver modulation energy in accordance with the modulation parameters, and receiving status information from the IPG 14; and input/output circuitry 70 for receiving modulation control signals from the button pad 54 or other control elements and transmitting status information to the display screen 52 (shown in FIG. 4). Further details of the functionality and internal componentry of the RC 16 are disclosed in U.S. Pat. No. 6,895,280, which has previously been incorporated herein by reference.

To allow the user to easily and quickly select between the different modes, the RC 16 comprises a modulation selection control element 63, which in the illustrated embodiment, takes the form of a button. The modulation selection control element 63 may be repeatedly actuated to toggle the IPG 14 between the super-threshold, sub-threshold, and hybrid delivery modes. For example, the modulation selection control element 63 may be actuated once to switch the IPG 14 from the super-threshold delivery mode to the sub-threshold delivery mode, actuated once again to switch the IPG 14 from the sub-threshold delivery mode to the hybrid delivery mode, actuated once again to switch the IPG 14 from the hybrid delivery mode back to the super-threshold delivery mode, and so forth. Of course, the order of the mode selection can be changed. For example, the modulation selection control element 63 may be actuated once to switch the IPG 14 from the sub-threshold delivery mode to the super-threshold delivery mode, actuated once again to switch the IPG 14 from the super-threshold delivery mode to the hybrid delivery mode, actuated once again to switch the IPG 14 from the hybrid delivery mode back to the sub-threshold delivery mode, and so forth. In any event, each of the modulation delivery modes can be selected by toggling the modulation selection control element 63.

Figure 6:
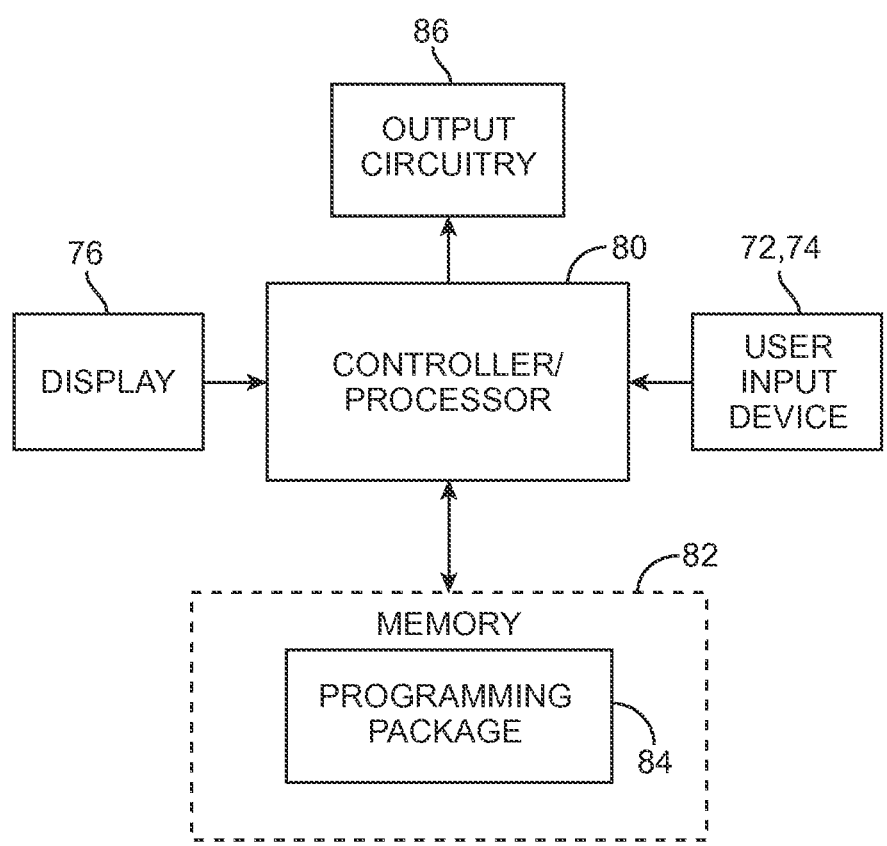
FIG. 6 is a block diagram of the internal components of a clinician's programmer (CP) used in the SCM system of Hg. 1.

As shown in FIG. 6, the CP 18 includes a controller/processor 80 (e.g., a central processor unit (CPU)) and memory 82 that stores a stimulation programming package 84, which can be executed by the controller/processor 80 to allow the user to program the IPG 14 and RC 16. The CP 18 further includes an output circuitry 86 for downloading modulation parameters to the IPG 14 and RC 16 and for uploading modulation parameters already stored in the memory 66 of the RC 16 or memory of the IPG 14. In addition, the CP 18 further includes a user input device 88 (such as the mouse 72 or keyboard 74) to provide user commands. Notably, while the controller/processor 80 is shown in FIG. 6 as a single device, the processing functions and controlling functions can be performed by a separate controller and processor 64. Thus, it can be appreciated that the controlling functions described below as being performed by the CP 18 can be performed by a controller, and the processing functions described below as being performed by the CP 18 can be performed by a processor.

After having described the SCM system 10 and its various components, exemplary RC 16 user interfaces and methods of using the SCM system 10 to (1) identify a perception threshold index, (2) generate new stimulation programs for the SCM system 10 using an identified perception threshold index, (3) modify existing stimulation programs for the SCM system 10 using an identified perception threshold index, and (4) batch modify existing stimulation programs for the SCM system 10 will now be described. The perception threshold is the lowest energy level at which a modulation signal causes a patient to feel paresthesia. The perception threshold changes with many variables, including: lead/electrode location, electrical field locus, electrical field focus, electrical field center point size, and patient physiology.

A modulation signal index is a function of a plurality of modulation signal parameters that is related to the energy of the modulation signal resulting from those modulation signal parameters. The "energy index" is an example of a modulation signal index, and is the product of amplitude, pulse width, and frequency/rate. Another example of a modulation signal index is the "charge index," which is the product of amplitude and pulse width. A modulation signal index for a modulation signal at a perception threshold is a perception threshold index. Expressing any modulation signal index as a percentage of the perception threshold index "normalizes" that modulation signal.

The perception threshold is identified with patient feedback. For instance, a series of modulation signals of incrementally increasing energy is delivered through a particular set of electrodes 26 implanted in a patient, and the SCM system 10 elicits and is configured to receive a voluntary input (e.g., a button press) from the patient when paresthesia is first perceived. The modulation index of the lowest energy modulation signal that causes a patient to perceive paresthesia is identified as the perception threshold index. Patient feedback may include both voluntary feedback and involuntary feedback based on a sensed physiological parameter indicative of super-threshold stimulation of the neural tissue (e.g., action potentials sensed by the IPG 14 at the particular set of electrodes 26 as a result of the delivery of the modulation energy). In the case of involuntary feedback, the perception threshold may be identified automatically, i.e., with minimal or no user input.

The SCM system 10 is programmed to identify a perception threshold index in a Perception Threshold Identification Mode. The SCM system 10 is also programmed to identify a maximum signal index, i.e., the modulation signal index representing the maximum signal strength before uncomfortable stimulation (e.g., pain) is perceived by the patient, in a Maximum Signal Identification Mode. Once the perception threshold index and the maximum signal index are identified, the RC 16 can be used to either generate new stimulation programs, or modify existing stimulation programs based on the perception threshold index in respective Program Generation Mode and Program Modification Mode. Using the perception threshold index to generate and modify stimulation programs increases usability by an end user, especially when that user is an untrained patient. The RC 16 indicates to the user the relative positions of the perception threshold, the maximum signal, and the stimulation programs. These quantitative maps provide a sense of scale that facilitates program generation and modification. The SCM system 10 may also perform a batch modification of a plurality of programs based on a changed perception threshold index, which may have resulted from lead 26 migration.

Figure 7A:
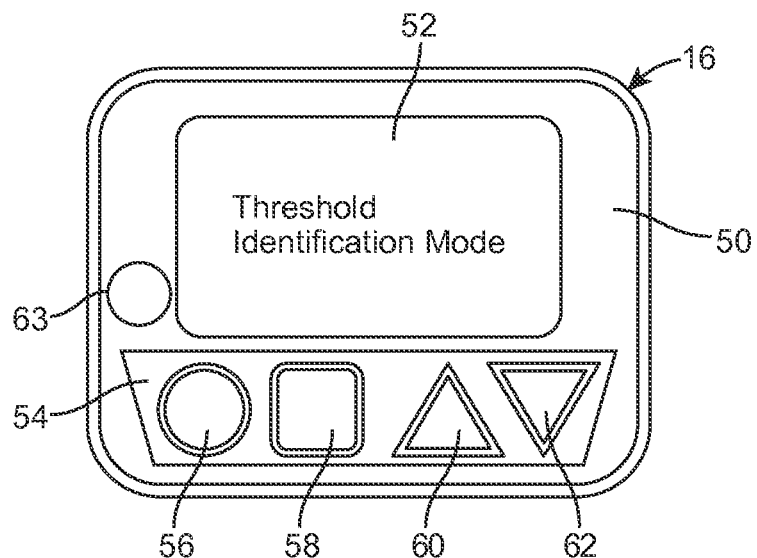
FIGS. 7A and 7B are plan views of a user interface of the RC of FIG. 4 for operating the IPG of FIG. 3 in a Perception Threshold Identification Mode.

A user (e.g., patient or clinician) can place the IPG 14 into Perception Threshold Identification Mode by repeatedly pressing the selection button 58 until the words "Threshold Identification Mode" are displayed in the display screen 52, as shown in FIG. 7A. Other events that may trigger the IPG 14 to enter Perception Threshold Identification Mode include a sensor signal indicating that one or more of the neuromodulation leads 12 has migrated relative to a target site in the patient, or a temporal occurrence, such as an elapsed time from a previous calibration procedure, a time of day, day of the week, etc.).

Once Perception Threshold Identification Mode is initiated, the RC 16 is configured for directing the IPG 14 to deliver the modulation energy to the electrodes 26 at incrementally increasing modulation signal indices, by incrementally and alternatively increasing the various numerical modulation signal parameters (e.g., amplitude, pulse width, duty cycle, and frequency/rate). Amplitude can be incrementally changed at a 0.1 mA step size. Pulse width can be incrementally changed at 10 µs or variable step size. Duty cycle can be incrementally changed at 1% or variable step size. Frequency/rate can be incrementally changed at a 1 Hz or variable step size. The modulation signal parameters are alternatively increased, for instance, by first increasing the amplitude by 0.1 mA, then increasing the pulse width by 10 µs or variable step size, then increasing the duty cycle by 5% or variable value, and then increasing the frequency/rate by next available step. Then the cycle of increasing modulation signal parameters is repeated starting with the amplitude. Alternatively, fewer than all of the numerical modulation signal parameters can be incrementally and alternatively increased to increase the modulation signal index.

The RC 16 may be configured for automatically incrementally increasing the modulation signal parameters of the electrical pulse train delivered by the IPG 14 without further user intervention or may be configured for incrementally increasing the modulation signal parameters of the electrical pulse train delivered by the IPG 14 each time the user actuates a control element, such as the up button 60.

The RC 16 is configured for prompting the user via the display 52 (shown in Hg. 7B) or speaker (not shown) to actuate a control element, such as a specified button 58 on the button pad 54 or another dedicated button (not shown), once paresthesia is perceived by the patient. In response to this user input, the RC 16 is configured to store the modulation signal index of the electrical pulse train delivered when the button 58 is pressed. This modulation signal index is identified as the perception threshold index for the particular lead location, electrical field locus, electrical field focus, and electrical field center point size.

Alternatively, rather than relying on voluntary user input, the RC 16 may be configured for automatically identifying the perception threshold index in response to a sensed physiological parameter indicative of super-threshold stimulation of the neural tissue (e.g., action potentials sensed by the IPG 14 at one or more electrodes 26 as a result of the delivery of the modulation energy). The above-described method for identifying a perception threshold index may be repeated to identify the perception threshold index at different axial/vertebral levels or for different electrode 26 sets.

Figure 7B:
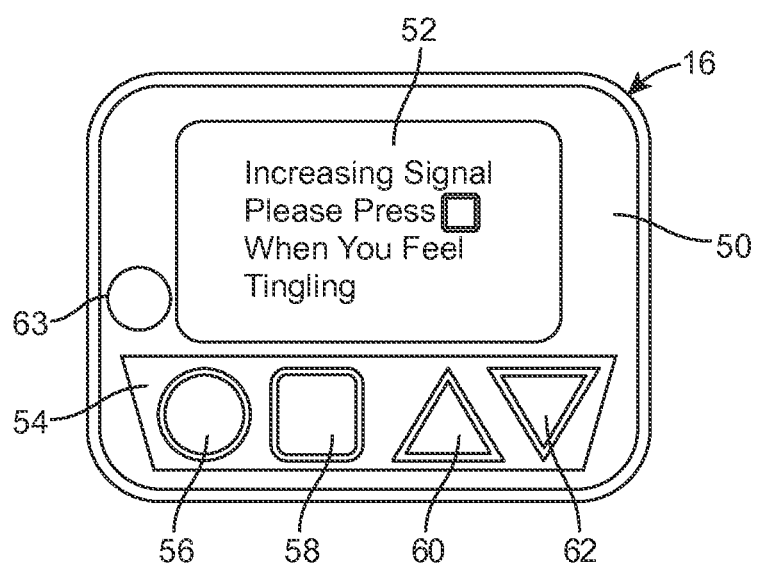
Figure 7C:
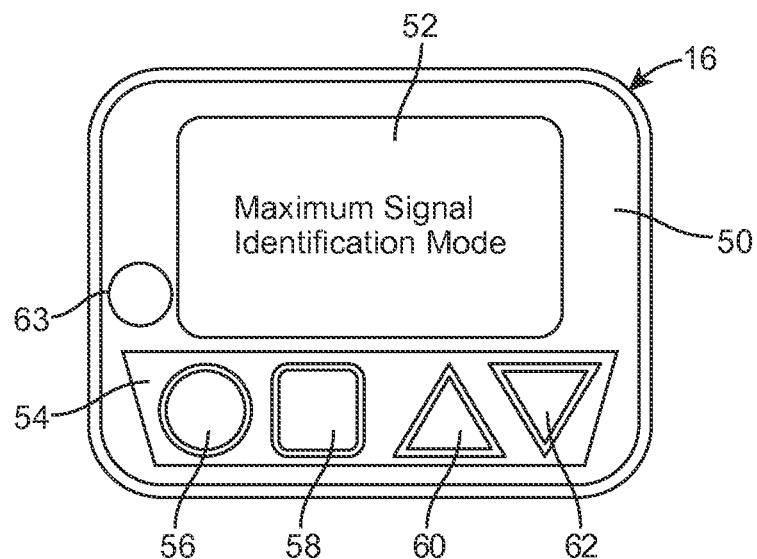
FIGS. 7C and 7D are plan views of a user interface of the RC of FIG. 4 for operating the IPG of FIG. 3 in a Maximum Signal Identification Mode.

A process similar to that described above for identifying the perception threshold index can also be used to identify a maximum signal index. For instance, after a perception threshold index has been determined, the user can place the IPG 14 into "Maximum Signal Identification Mode" by pressing the selection button 58 until the words "Maximum Signal Identification Mode" are displayed in the display screen 52, as shown in FIG. 7C.

Once Maximum Signal Identification Mode is initiated, the RC 16 is configured for directing the IPG 14 to deliver the modulation energy to the electrodes 26 at incrementally increasing modulation signal indices, starting at the perception threshold index. The RC 16 is configured for prompting the user via the display 52 (shown in FIG. 7D) or speaker (not shown) to actuate a control element, such as a specified button 58 on the button pad 54 or another dedicated button (not shown), once uncomfortable stimulation (e.g., pain) is perceived by the patient. In response to this user input, the RC 16 is configured to store the modulation signal index of the electrical pulse train delivered when the button 58 is pressed. This modulation signal index is identified as the maximum signal index for the particular lead location, electrical field locus, electrical field focus, and electrical field center point size.

Figure 7D:
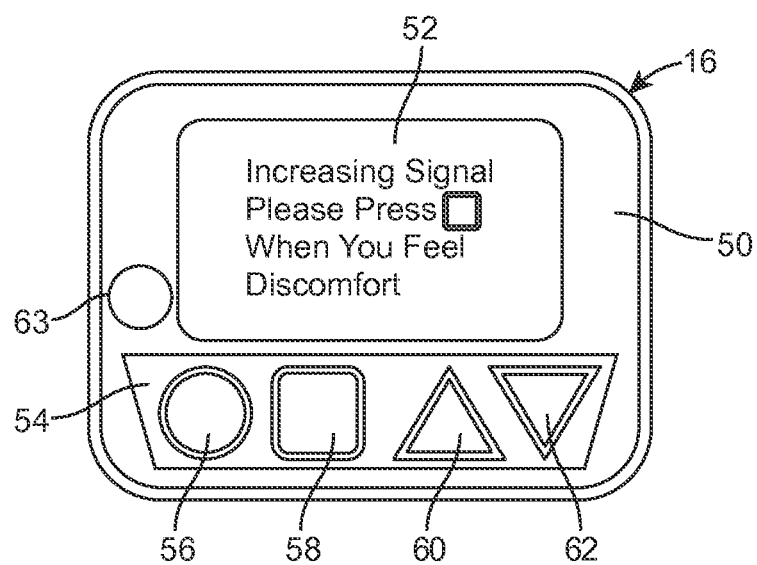
Figure 7E:
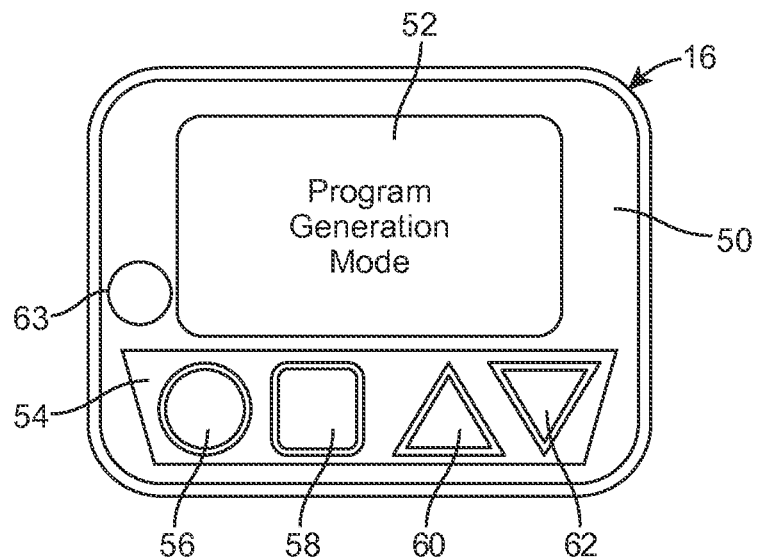
FIGS. 7E to 7J are plan views of a user interface of the RC of FIG. 4 for programming the IPG of FIG. 3 in a Program Generation Mode.
Figure 7F:
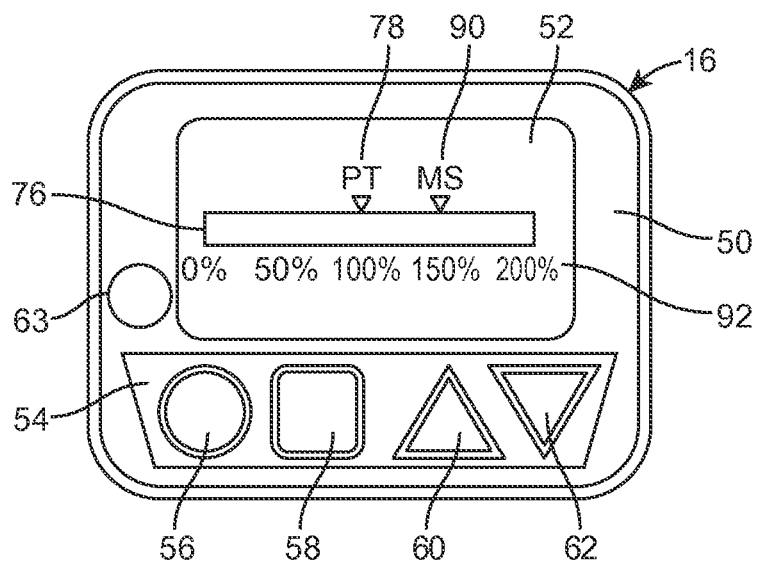

A user can place the IPG 14 into Program Generation Mode by repeatedly pressing the selection button 58 until the words "Program Generation Mode" are displayed in the display screen 52, as depicted in FIG. 7E. In the Program Generation Mode, the RC 16 is programmed to present a sliding scale user interface 76 on the display 52 that identifies the perception threshold index with an indicator 78 thereon, as illustrated in FIG. 7F. The indicator 78 includes the letters "PT" to identify indicator 78 as the perception threshold index indicator. The sliding scale user interface 76 can also include another indicator 90 that identifies the maximum signal index. This other indicator 90 includes the letters "MS" to identify indicator 90 as the maximum signal index indicator. The sliding scale user interface 76 is graduated with a scale 92 with units based on a percentage of the perception threshold index. In the illustrated embodiment, the scale starts at 0% and increases to 200% of the perception threshold index.

In FIG. 7F, the perception threshold indicator 78 is fixed at 100% and the maximum signal indicator 90 has been set to 150%. The location of the maximum signal indicator 90 illustrates that the maximum signal index has been determined to be 150% of the perception threshold index in the Maximum Signal Identification Mode. Therefore, the normalized value of the maximum signal index is 150% of the perception threshold index.

Figure 7G:
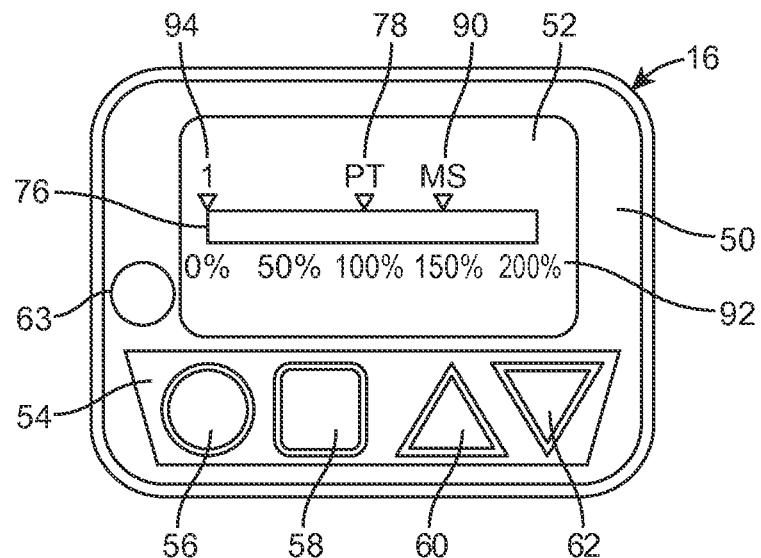
Figure 7H:
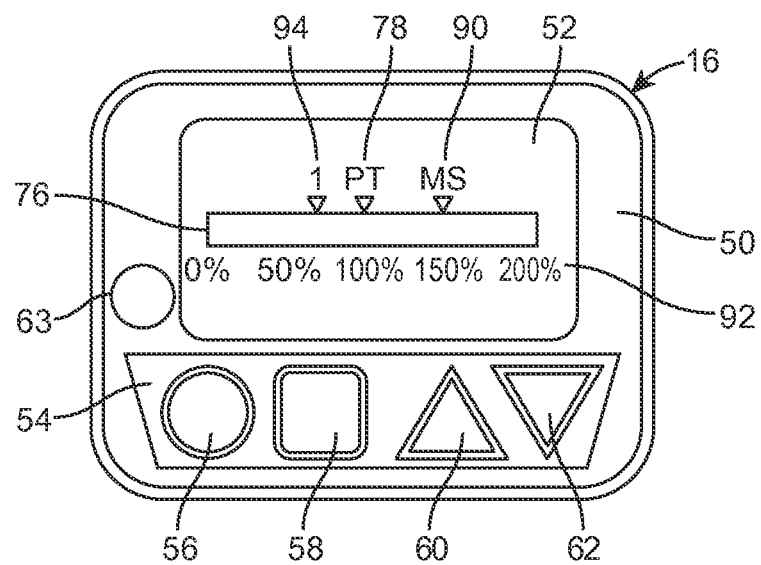
Figure 7I:
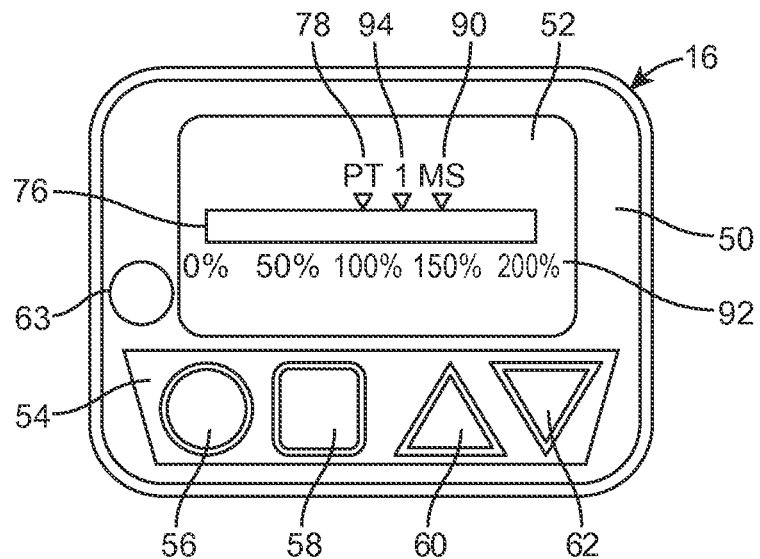

With the perception threshold index identified, stored, and displayed in the display screen 52, the user can use the perception threshold index to generate a new stimulation program. The user can press the up button 60 to begin generating a new stimulation program. In response to the up button 60 press, a new indicator 94 is displayed, as shown in FIG. 7G. This first program indicator 94 includes the number "1" to identify indicator 94 as representative of a first newly generated stimulation program. The new indicator 94 depicts the modulation signal index of the new program as a normalized function of the perception threshold index, and is initially set at 0%. Repeatedly pressing the up button 60 incrementally increases the modulation signal index of the new program as described above. For an energy index, repeatedly pressing the up button 60 can incrementally and alternatively increase the amplitude, pulse width, and frequency/rate of the modulation parameter set for the new program. As shown in FIG. 7H, a user can set the modulation signal index below the perception threshold index (e.g., 75%) for a sub-threshold stimulation program. Alternatively, as shown in FIG. 7I, a user can set the modulation signal index above the perception threshold index (e.g., 125%) for a super-threshold stimulation program. This process can be repeated to generate additional stimulation programs. The RC 16 can also be configured to disable setting any program indicator to a value higher than the maximum signal index.

Figure 7J:
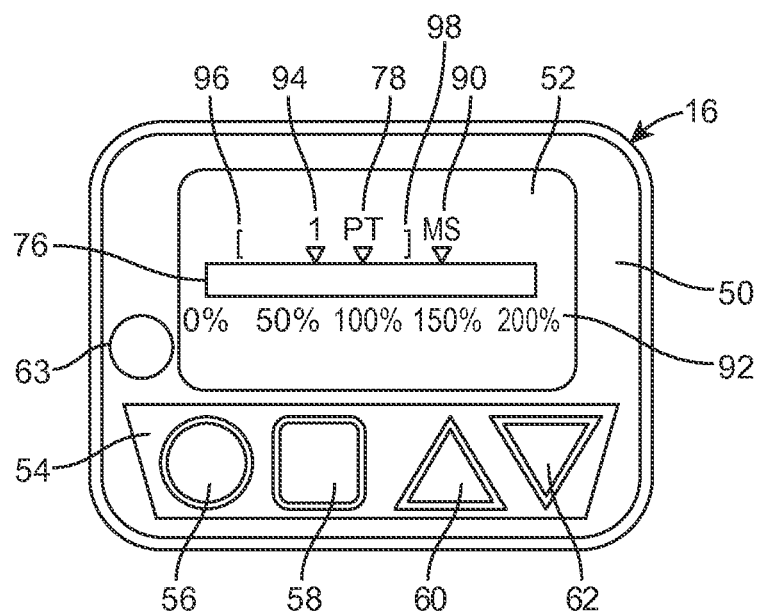

A user can also establish minimum and maximum values for modulation indices. As depicted in FIG. 7J, the minimum and maximum values are depicted by right facing and left facing bracket indicators 96, 98, respectively. These minimum and maximum value indicators 96, 98 restrict the minimum and maximum modulation energies for stimulation programs, thereby avoiding ineffective and painful stimulation signals, respectively. In FIG. 7J, the minimum and maximum value indicators 96, 98 have been set at normalized values of 25% and 140% of the perception threshold index, respectively.

The Perception Threshold Identification Mode (depicted in FIGS. 7A and 7B), the Maximum Signal Identification Mode (depicted in FIGS. 7C and 7D), and the Program Generation Mode (depicted in FIGS. 7E to 7J) can be used to generate stimulation programs based on a perception threshold index. As shown in Hg 8, a method of generating a stimulation program based on a perception threshold index begins with identifying a patient's perception threshold index using the RC 16 in the Perception Threshold Identification Mode, at step 102. Optionally, a maximum signal index can be identified using the RC 16 in the Maximum Signal Identification Mode, and step 104. Next, the RC 16 can be placed in Program Generation Mode at step 106. In the Program Generation Mode, a program indicator 94 is initially displayed at 0% normalized to the perception threshold index on the sliding scale user interface 76, as shown in Hg. 7G. Finally, the program indicator 94 is moved along the sliding scale user interface 76 to set the modulation index of the new program, at step 108.

Figure 7K:
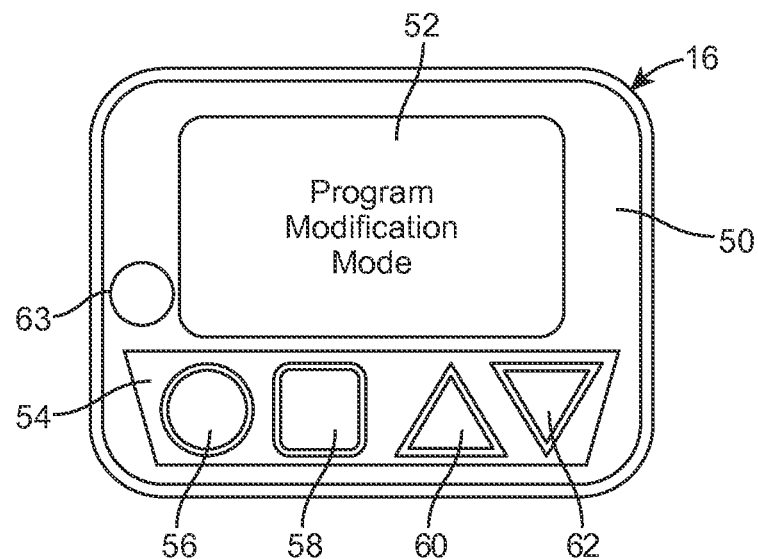
FIGS. 7K to 7M are plan views of a user interface of the RC of FIG. 4 for programming the IPG of Hg. 3 in a Program Modification Mode.

A user can place the IPG 14 into Program Modification Mode by repeatedly pressing the selection button 58 until the words "Program Modification Mode" are displayed in the display screen 52, as depicted in FIG. 7K, in Program Modification Mode (shown in FIG. 7L), the RC 16 is programmed to present a sliding scale user interface 76 on the display 52 similar to the one depicted in FIG. 7F. The sliding scale user interface 76 also includes the perception threshold index indicator 78, the maximum signal index indicator 90, and the minimum and maximum value indicators 96, 98, if any, as described above. The RC 16 is also programmed to present one or more program indicators 94, is also described above. In the embodiment depicted in Hg. 7L, the IPG 14 has three programs, and, accordingly, the RC 16 displays three program indicators 94. Each of the program indicators 94 includes a number above the indicator 94 to distinguish the program indicators from each other and the other indicators on the display 52.

In Program Modification Mode, a user can modify any of the displayed programs by selecting the appropriate program indicator 94 and adjusting the modulation signal index of the program up or down relative to the perception threshold index. For instance, as shown in Hg. 7M, the modulation signal index of program one has been increased from 80% to 120% by moving the corresponding program indicator 94.

Figure 7L:
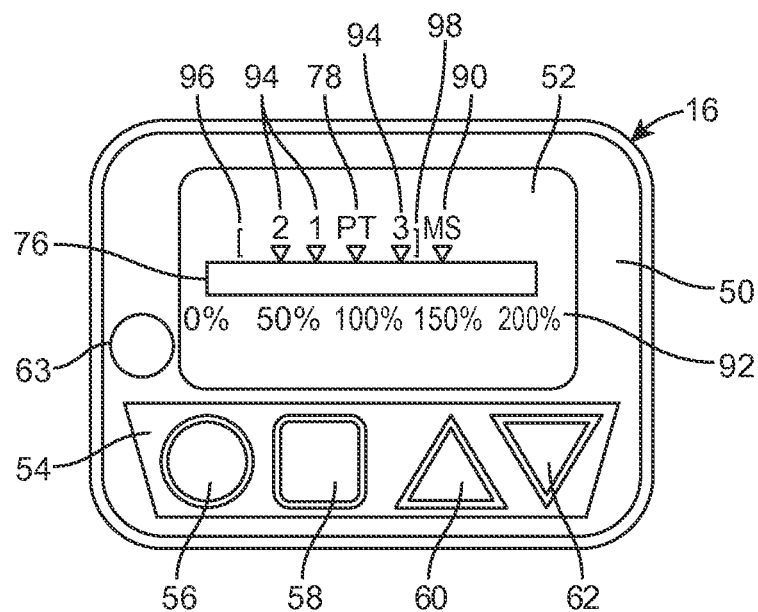
Figure 7M:
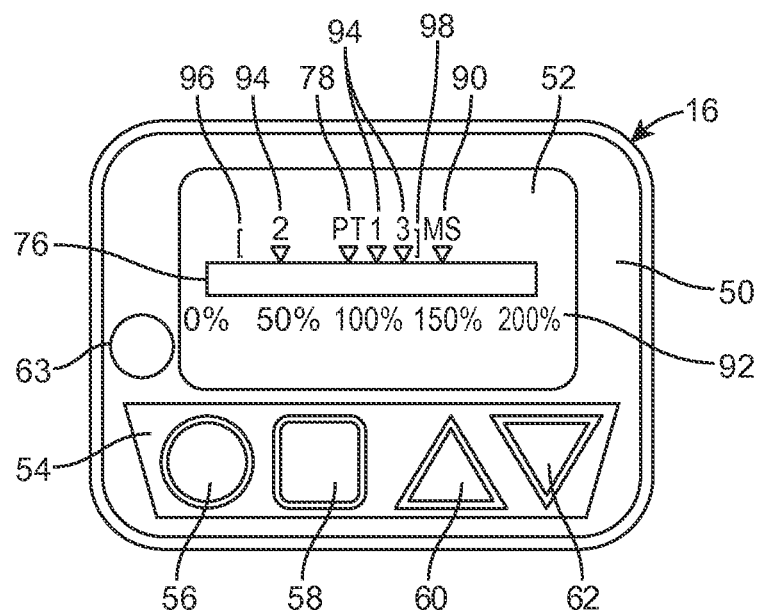
Figure 9:
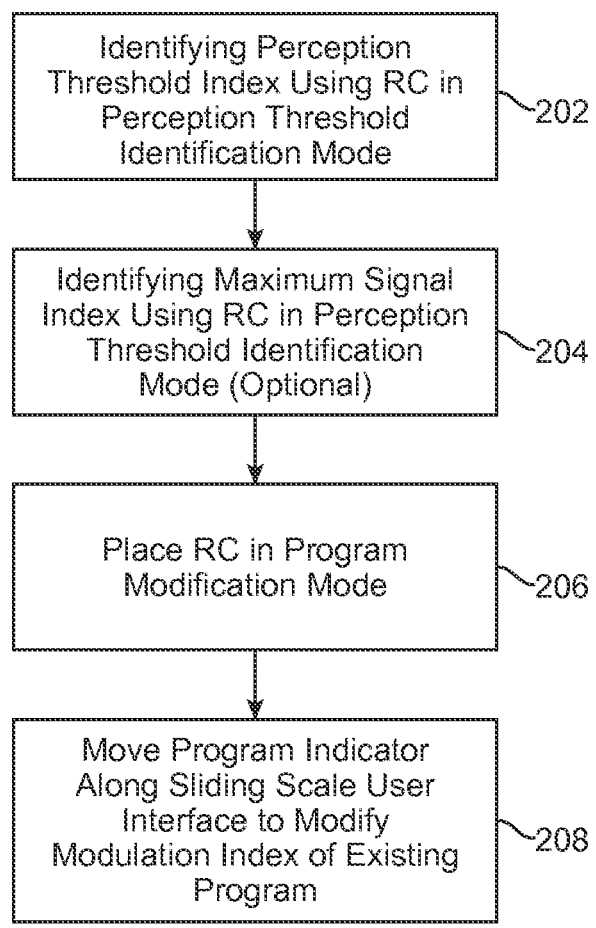
FIG. 9 is a flow diagram illustrating steps for using the RC of FIG. 4 to modify programs in the IPG of FIG. 3 in a Program Modification Mode.

The Perception Threshold Identification Mode (depicted in FIGS. 7A and 7B), the Maximum Signal Identification Mode (depicted in FIGS. 7C and 7D), and the Program Modification Mode (depicted in FIGS. 7K to 7M) can be used to modify stimulation programs based on a perception threshold index. As shown in FIG. 9, a method of modifying a stimulation program based on a perception threshold index begins with identifying a patient's perception threshold index using the RC 16 in the Perception Threshold Identification Mode, at step 202. Optionally, a maximum signal index can be identified using the RC 16 in the Maximum Signal Identification Mode, and step 204. Next, the RC 16 can be placed in Program Modification Mode at step 206. In the Program Modification Mode, a program indicator 94 is initially displayed at the modulation index of the program. For instance, the indicator 94 for program 1 is initially displayed at 0% normalized to the perception threshold index on the sliding scale user interface 76, as shown in FIG. 7L. Finally, the program indicator 94 is moved along the sliding scale user interface 76 to modify the modulation index of the existing program, at step 208. For instance, the indicator for program 1 has been moved to 120% normalized to the perception threshold index, as shown in FIG. 7M.

As mentioned above, the perception threshold may change with lead/electrode location. In addition to changing the leads and electrodes used to deliver a modulation signal, lead/electrode location may also change when implanted modulation lead(s) 12 migrate relative a target tissue site in the patient. Causes of lead migration include patient activity and postural changes. When lead migration changes the perception threshold, one or more stimulation signals from the migrated modulation lead(s) 12 may fall outside of the therapeutic range. Migration of the modulation lead(s) 12 may alter the coupling efficiency between the modulation lead(s) 12 and the target tissue site. A decreased coupling efficiency may cause the stimulation therapy to fall below the therapeutic range and result in ineffective therapy. An increased coupling efficiency may cause the stimulation therapy to rise above the therapeutic range, and result in the perception of paresthesia or pain, or otherwise inefficient energy consumption. To compensate for the altered coupling efficiency, the SCM system 10 identifies a new perception threshold, which can be used to generate new stimulation programs or modify existing stimulation programs as described below.

Figure 7N:
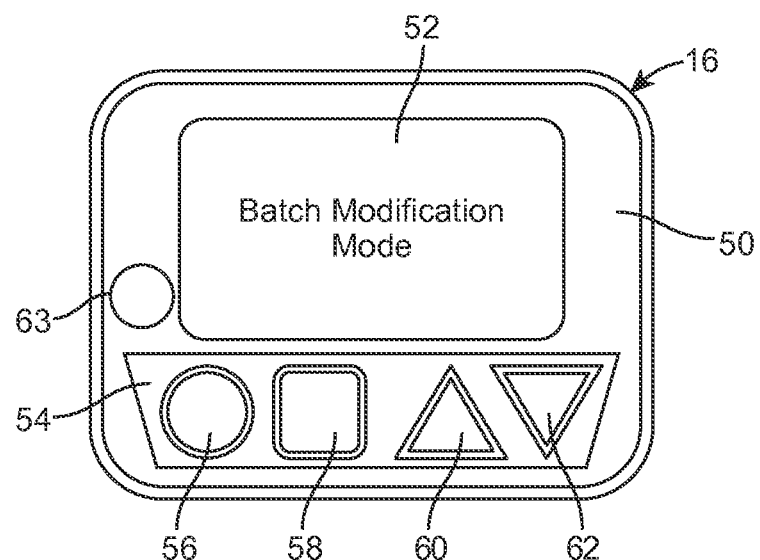
FIGS. 7N and 7O are plan views of a user interface of the RC of FIG. 4 for programming the IPG of FIG. 3 in a Batch Program Modification Mode.
Figure 7O:
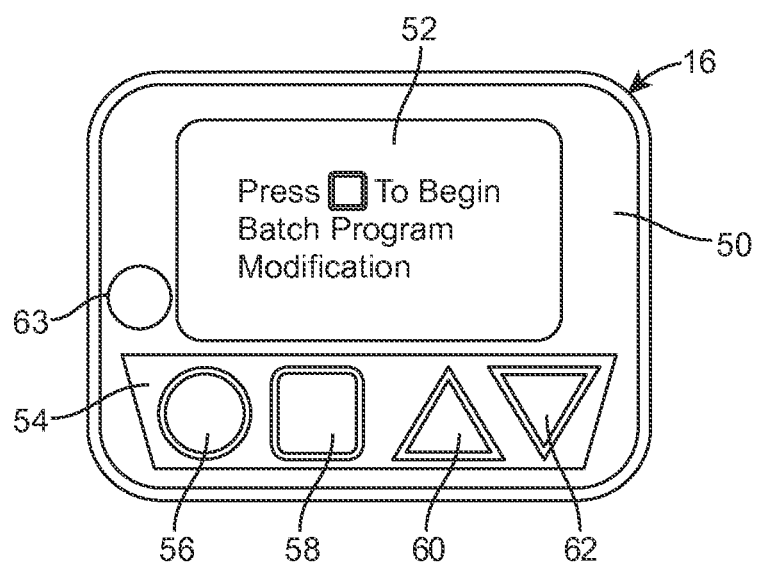
Figure 8:
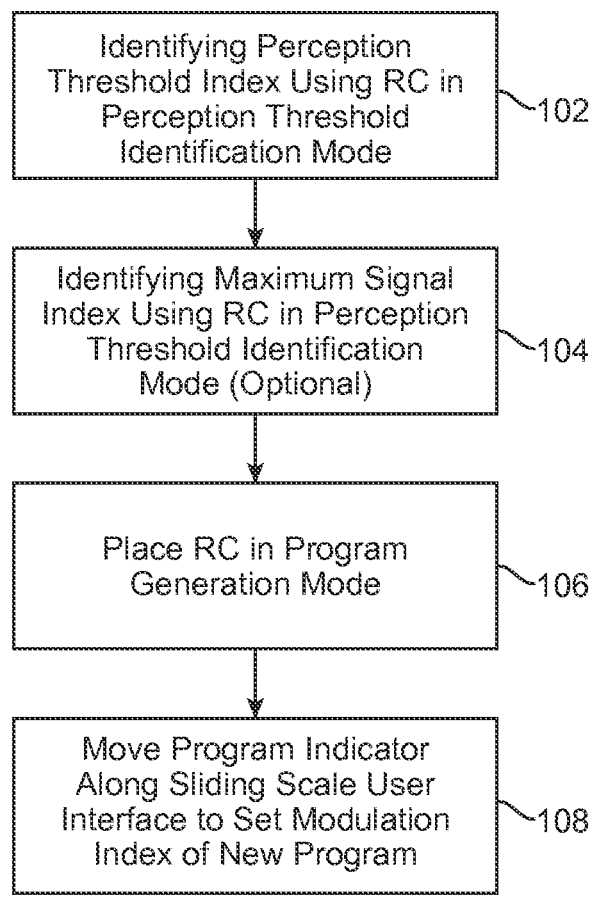
FIG. 8 is a flow diagram illustrating steps for using the RC of FIG. 4 to program the IPG of FIG. 3 in a Program Generation Mode.

Stimulation programs that either lose their effectiveness or begin to cause unwanted paresthesia or pain indicate that one or more modulation leads 26 may have shifted, leading to altered coupling efficiency, and a changed perception index. The Batch Program Modification Mode may be used to compensate for lead 26 migration. A user can place the IPG 14 into Batch Program Modification Mode by repeatedly pressing the selection button 58 until the words "Batch Modification Mode" are displayed in the display screen 52, as depicted in FIG. 7N. The Batch Program Modification Mode is an automatic or semi-automatic mode, in which the RC 16 prompts the user via the display 52 (shown in FIG. 7O) or speaker (not shown) to actuate a control element, such as a specified button 58 on the button pad 54 or another dedicated button (not shown), to begin batch program modification.

Figure 10:
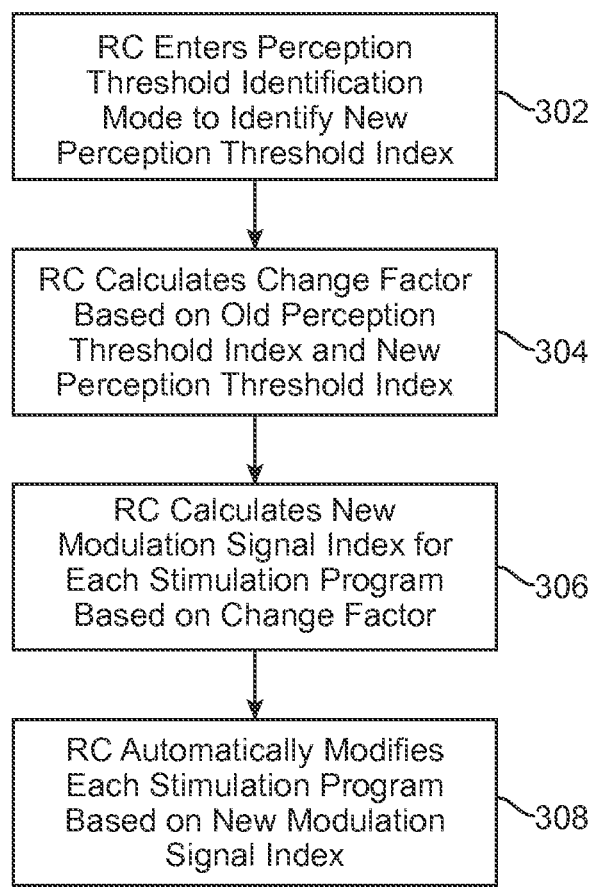
FIG. 10 is a flow diagram illustrating steps for using the RC of FIG. 4 to modify programs in the IPG of FIG. 3 Batch Program Modification Mode.

As shown in FIG. 10, batch program modification, beings with the RC 16 entering Perception Threshold Identification Mode at step 302, as shown in FIGS. 7A and 7D and described above, to identify a new (changed) perception threshold index. Then the RC 16 compares the old perception threshold index with the new (changed) perception threshold index at step 304 to calculate a factor indicative of the change to the perception threshold index. For instance, the RC 16 can divide the new perception threshold index by the old perception threshold index to calculate the factor.

The RC 16 then automatically computes a new modulation signal index for each stimulation program on the IPG 14, at step 306, by multiplying their respective old modulation signal indices by the calculated factor. At step 308, the RC 16 automatically modifies the modulation signal parameters of each stimulation program on the IPG 14 to adjust their respective modulation signal indices to the respective computed new modulation signal indices, as described above. The RC 16 can optionally seek user confirmation before modifying the modulation signal parameters.

While the Perception Threshold Identification Mode (depicted in FIGS. 7A and 7B), the Maximum Signal Identification Mode (depicted in FIGS. 7C and 7D), the Program Generation Mode (depicted in FIGS. 7E to 7J), the Program Modification Mode (depicted in FIGS. 7K to 7M), and the Batch Program Modification Mode (depicted in FIGS. 7E to 7J) have been depicted as executable using the RC 16, these programming modes and methods can also be executed on the CP 18 to facilitate clinician programming and modification of stimulation programs. Although clinicians are trained to manipulate the various modulation parameters, the various indicators 78, 90, 94, 96, 98 on the sliding scale user interface 76 provide a sense of relative scale of the perception threshold index, the maximum signal index, and the stimulation program index. These visual cues aid both the clinician (using a CP 18 or an RC 16) and a patient (using an RC 16) in programming the IPG 14.

Although particular embodiments of the present inventions have been shown and described, it will be understood that it is not intended to limit the present inventions to the preferred embodiments, and it will be obvious to those skilled in the art that various changes and modifications may be made without departing Thorn the spirit and scope of the present inventions. Thus, the present inventions are intended to cover alternatives, modifications, and equivalents, which may be included within the spirit and scope of the present inventions as defined by the claims.

What is claimed is:

1. A method of operating an implantable neuromodulator coupled to an electrode array implanted adjacent tissue of a patient having a medical condition, comprising:
    calculating an index for each of a plurality of modulation parameter sets to provide each of the plurality of modulation parameter sets with a respective calculated index, wherein each modulation parameter set includes a respective plurality of modulation parameters, and wherein the respective calculated index for each of the plurality of modulation parameter sets is calculated as a function of the respective plurality of modulation parameters;
    serially conveying electrical modulation energy to the tissue in accordance with each of the plurality of modulation parameter sets;
    causing the patient to perceive paresthesia in response to the conveyance of the electrical modulation energy to the tissue in accordance with one of the plurality of modulation parameter sets;
    identifying the respective calculated index for the one of the plurality of modulation parameter sets as a perception threshold index based on the perceived paresthesia;
    storing the identified perception threshold index;
    determining a new modulation parameter set for a sub-threshold therapy based on the identified perception threshold index; and
    delivering the sub-threshold therapy, including conveying sub-threshold electrical modulation energy to the tissue in accordance with the new modulation parameter set.

2. The method of claim 1, wherein determining a new modulation parameter set based on the identified perception threshold index comprises
    selecting a new index by applying a function to the identified perception index; and
    determining a plurality of modulation parameters based on the new index.

3. The method of claim 1, further comprising modifying a modulation parameter set based on the identified perception threshold index, and conveying electrical modulation energy to the tissue in accordance with the modified modulation parameter set, wherein modifying a modulation parameter set based on the identified perception threshold index comprises
    selecting a new index by applying a function to the identified perception index; and
    determining a plurality of modulation parameters based on the new index.

4. The method of claim 1, wherein the plurality of modulation parameters used to calculate the index includes two or more modulation parameters selected from the group consisting of amplitude, pulse width, duty cycle, frequency, lead location, electrical field locus, electrical field focus, and electrical field center point size.

5. The method of claim 1, wherein:
    each of the plurality of modulation parameter sets directs the implantable neuromodulator to convey electrical modulation energy at a first axial level, the method further comprising identifying another perception threshold index for electrical modulation energy conveyed at a second axial level.

6. The method of claim 1, wherein each of the plurality of modulation parameter sets directs the implantable neuromodulator to convey electrical modulation energy through a first electrode, the method further comprising identifying another perception threshold index for electrical modulation energy conveyed through a second electrode.

7. The method of claim 1, further comprising:
    causing the patient to perceive paresthesia in response to the conveyance of the electrical modulation energy to the tissue in accordance with more than one of the plurality of modulation parameter sets; and
    identifying the lowest calculated index for the more than one of the plurality of modulation parameter sets as the perception threshold index based on the perceived paresthesia.

8. The method of claim 1, wherein the index is an energy index calculated by multiplying respective an amplitude, a pulse width, and a frequency.

9. The method of claim 2, wherein conveying electrical modulation energy to the tissue in accordance with the new modulation parameter set comprises conveying super-threshold electrical modulation energy.

10. A method of operating an implantable neuromodulator coupled to an electrode array implanted adjacent tissue of a patient having a medical condition, comprising:

calculating an index for each of a plurality of modulation parameter sets to provide each of the plurality of modulation parameter sets with a respective calculated index, wherein each modulation parameter set includes a respective plurality of modulation parameters, and wherein the respective calculated index for each of the plurality of modulation parameter sets is calculated as a function of the respective plurality of modulation parameters, wherein calculating the index includes:
calculating an energy index as a product of amplitude, pulse width and frequency; or
calculating a charge index as a product of amplitude and pulse width;
serially conveying electrical modulation energy to the tissue in accordance with each of the plurality of modulation parameter sets;
causing the patient to perceive paresthesia in response to the conveyance of the electrical modulation energy to the tissue in accordance with one of the plurality of modulation parameter sets;
identifying the respective calculated index for the one of the plurality of modulation parameter sets as a perception threshold index based on the perceived paresthesia;
storing the identified perception threshold index;
determining a new modulation parameter set for a sub-threshold therapy based on the identified perception threshold index; and
delivering the sub-threshold therapy, including conveying sub-threshold electrical modulation energy to the tissue in accordance with the new modulation parameter set.

11. The method of claim 10, further comprising determining a new modulation parameter set based on the identified perception threshold index, and conveying electrical modulation energy to the tissue in accordance with the new modulation parameter set.

12. The method of claim 11, wherein determining a new modulation parameter set based on the identified perception threshold index comprises selecting a new index by applying a function to the identified perception index; and
determining a plurality of modulation parameters based on the new index.

13. The method of claim 11, wherein conveying electrical modulation energy to the tissue in accordance with the new modulation parameter set comprises conveying sub-threshold electrical modulation energy.

14. The method of claim 11, wherein conveying electrical modulation energy to the tissue in accordance with the new modulation parameter set comprises conveying super-threshold electrical modulation energy.

15. The method of claim 11, further comprising modifying a modulation parameter set based on the identified perception threshold index, and conveying electrical modulation energy to the tissue in accordance with the modified modulation parameter set, wherein modifying a modulation parameter set based on the identified perception threshold index comprises selecting a new index by applying a function to the identified perception index; and
determining a plurality of modulation parameters based on the new index.

16. The method of claim 10, wherein:
each of the plurality of modulation parameter sets directs the implantable neuromodulator to convey electrical modulation energy at a first axial level, the method further comprising identifying another perception threshold index for electrical modulation energy conveyed at a second axial level.

17. The method of claim 10, wherein each of the plurality of modulation parameter sets directs the implantable neuromodulator to convey electrical modulation energy through a first electrode, the method further comprising identifying another perception threshold index for electrical modulation energy conveyed through a second electrode.

18. The method of claim 10, further comprising:
causing the patient to perceive paresthesia in response to the conveyance of the electrical modulation energy to the tissue in accordance with more than one of the plurality of modulation parameter sets; and
identifying the lowest calculated index for the more than one of the plurality of modulation parameter sets as the perception threshold index based on the perceived paresthesia.

* * * * *